United States Patent [19]
Gratton et al.

[11] Patent Number: 5,212,386
[45] Date of Patent: May 18, 1993

[54] HIGH SPEED CROSS-CORRELATION FREQUENCY DOMAIN FLUOROMETRY-PHOSPHORIMETRY

[75] Inventors: Enrico Gratton, Urbana; Beniamino Barbieri, Champaign, both of Ill.

[73] Assignee: I.S.S. (U.S.A.) Inc., Champaign, Ill.

[21] Appl. No.: 807,261

[22] Filed: Dec. 13, 1991

[51] Int. Cl.$^5$ ............................................. G01N 21/64
[52] U.S. Cl. .............................. 250/458.1; 250/459.1; 356/317; 356/318
[58] Field of Search ............... 250/458.1, 459.1, 461.1, 250/461.2; 356/317, 318, 417

[56]  References Cited
U.S. PATENT DOCUMENTS
4,840,485  6/1989  Gratton ............................. 250/458.1
4,937,457  6/1990  Mitchell ............................ 250/458.1

OTHER PUBLICATIONS

Article by B. A. Feddersen et al. entitled Digital Parallel Acquisition in Frequency Domain Fluorimetry, Rev. Sci. Instrum. 60(9), Sep., 1989 pp. 2929-2936.
Article by Beniamino Barbieri et al. entitled Synthesizers' Phase Noise in Frequency-Domain Fluorometry, Rev. Sci. Instrum. 60(10), Oct., 1989, pp. 3201-3206.
Article by Brett Feddersen et al. entitled Direct Waveform Collection and Analysis of Phase Fluorometry Data, Biophysical Journal 53 (2) 404a (1988) consisting of 10 pages.
Article by Enrico Gratton et al. entitled A Continuously Variable Frequency Cross-Correlation Phase Fluorometer With Picosecond Resolution, Biophysical Journal, vol. 44, pp. 315-324 (1983).

Primary Examiner—Carolyn E. Fields
Attorney, Agent, or Firm—Gerstman & Ellis, Ltd.

[57] ABSTRACT

Apparatus for cross-correlation frequency domain fluorometry and/or phosphorimetry in which means are provided for sequentially performing runs of the cross correlation frequency domain fluorometry and/or phosphorimetry at sequentially differing first and second frequencies. The intensities of signal responses of the runs are detected at the respective cross-correlation frequency in each run. The detection of the signal response is prolonged in each run until an integrated signal with a specified standard deviation has been acquired at each of the differing runs. Preferably the sequential runs are automatically executed by a program. Also, the waveforms sensed by deriving the resultant signal response in each run are folded. That is: corresponding segments of the waveforms are superimposed to obtain an average waveform value for each run having an increased signal to noise ratio over the individual waveform segments. Also, preferably, a software-created variable frequency digital filter is used to filter signal responses at the cross-correlation frequency.

27 Claims, 6 Drawing Sheets

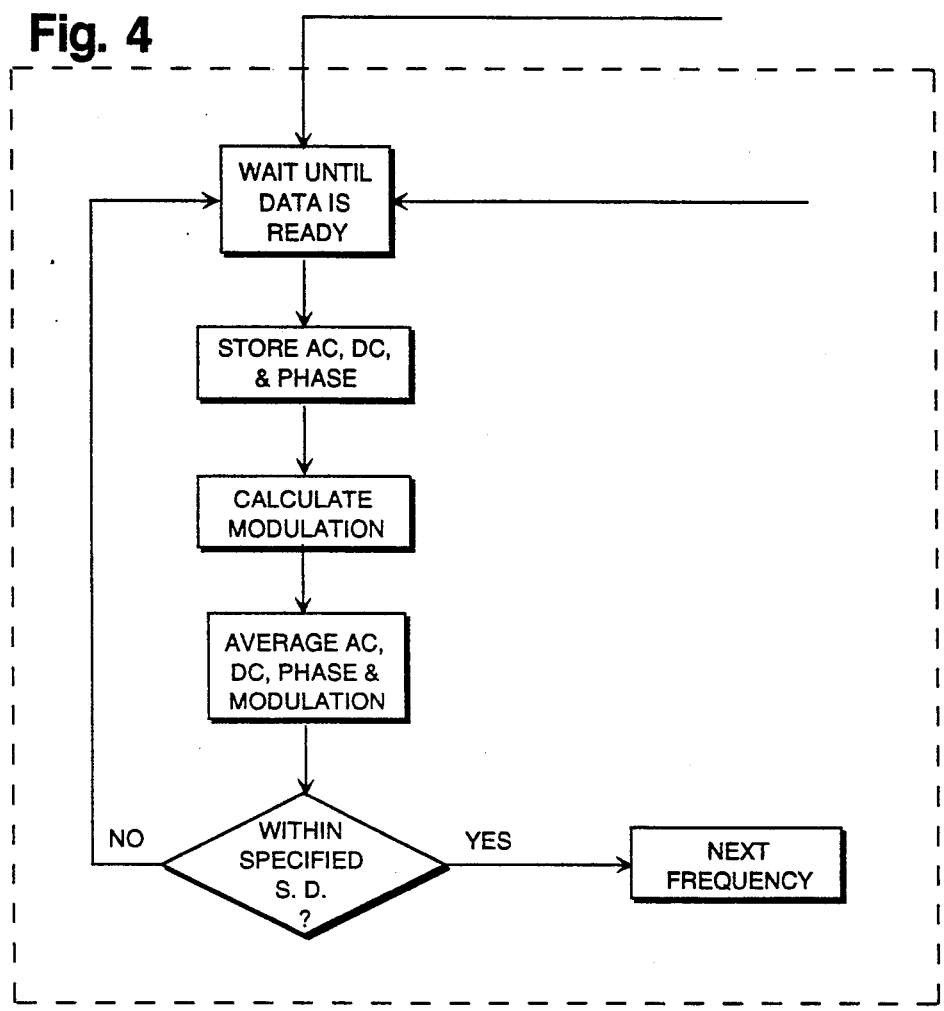
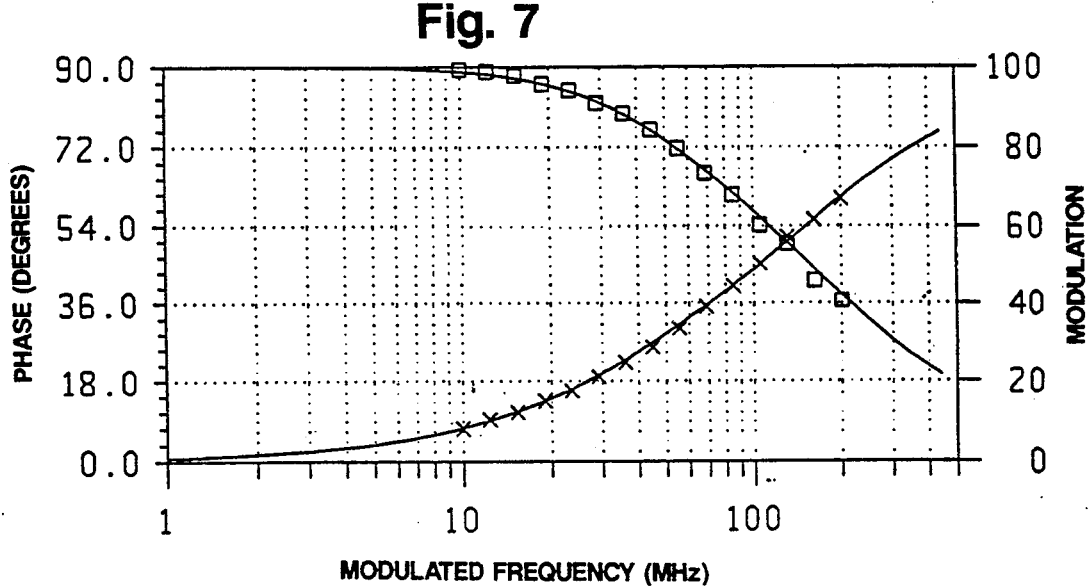

5,212,386

HIGH SPEED CROSS-CORRELATION FREQUENCY DOMAIN FLUOROMETRY-PHOSPHORIMETRY

BACKGROUND OF THE INVENTION

The invention herein relates to an improved form of cross-correlation frequency domain fluorometry and/or phosphorimetry. This process is well-known per se, being as described, for example, in Gratton U.S. Pat. No. 4,840,485, and also in a large body of technical literature on the subject. Also, instruments for performing this process are sold by I.S.S. Inc., of 309 Windsor Road, Champaign, Ill. 61820, among others.

Instruments for performing the above processes are utilized for measurement of the fluorescence decay, phosphorescence decay, anisotropy decay of fluorescence or phosphorescence, and other known uses. These instruments differ from the more common steady-state spectrofluorometers since they provide a means to record the time evolution of the deactivation of molecules or atoms after excitation with light. Typical times involved in these processes span from 1 millisecond to 1 picosecond. Such frequency domain fluorometers (which term is intended to include corresponding phosphorimeters) are also utilized for the measurement of times involved in other molecular dynamic processes such as the rotations of molecules or parts of large molecules. Also, the apparatus may be used for the resolution of excitation/emission spectra of different fluorescence or phosphorescence molecules in a mixture; for the determination of time-resolved spectra; for the resolution of kinetics decays of fluorophores in a mixture; or for the measurement of reactions occurring in the electronic excited state.

In a frequency domain fluorometer, the excitation light beam causing fluorescent emission is amplitude-modulated by a light modulator, such as a Pockels cell, or it is intrinsically modulated when the source is a mode-locked laser or synchrotron radiation source. The fluorescence emission is phase-shifted and demodulated with respect to the excitation light beam. The shift in the phase and the demodulation are both related to the lifetime of the excited electronic level of the emitting molecule or atom, providing a means to determine the modalities of the decay.

Two types of frequency domain fluorometers are commercially available at this time:

In a first type of instrument, the excitation light beam is modulated at a certain frequency F, generally in the 0.1 KHz to 300 MHz range. The phase shift and the demodulation of the fluorescence or phosphorescence are measured using the cross-correlation technique. Measurements are repeated at different modulation frequencies, usually 10 to 20 different frequencies which are logarithmically spaced in a desired frequency interval which depends on the characteristic decay time of the fluorescent or phosphorescent molecule under investigation. This type of instrument is referred to in the literature as a "serial" frequency domain fluorometer, since the various measurements at different modulation frequencies are made in a sequence of time, one after the other.

Several models of such serial fluorometers are commercially available, for example the K2 introduced by I.S.S. in 1989 and the SLM 48000, marked by SLM Instruments. Data acquisition with instruments belonging to this class usually take from one-half hour to one hour for the collection of 10 to 20 different frequencies. These instruments offer the best sensitivity, which is an important factor when working with substance having a low fluorescence quantum yield or substances in low concentration such as proteins or other biological materials. Similarly, these instruments measure in a differential way the rotational rates of molecules without the necessity of deconvolution techniques.

A second type of instrument has also been introduced to the market, as described by Mitchell U.S. Pat. No. 4,937,457 and entitled Picosecond Multiharmonic Fourier Fluorometer. This instrument si referred to as a "parallel" frequency domain fluorometer, since data are acquired simultaneously at different modulation frequencies. Usually, about 100 different modulation frequencies are acquired simultaneously. This type of instrument can potentially reduce the acquisition time by an order of magnitude, but as a disadvantage it has very low sensitivity. The advantage obtained by the reduction in data acquisition time is thus offset by the fact that the system is only capable of studying systems with a very strong fluorescent signal. When the signal is low, which is the case encountered in most applications involving biological materials, the only way to get reasonable data from this kind of instrument is to increase the data acquisition time. Therefore, in many instances the instrument does not offer any tangible advantage over a standard serial instrument.

Also, the parallel type frequency domain fluorometer is inherently more expensive, which provides further disadvantage.

Parallel frequency domain fluorometry is described in the article by B. A. Feddersen et al. entitled Digital Parallel Acquisition in Frequency Domain Fluorometry, Rev. Sci. Instrum. Vol. 60 (1989) page 2929–2936.

By this invention, a new type of cross-correlation frequency domain fluorometer and/or phosphorimeter is provided which has a significantly reduced time required for the acquisition of a good signal having a high signal to noise ratio, when compared with the standard serial-type fluorometers. However, the apparatus of this invention also retains the high sensitivity to faint signals of serial fluorometry, while providing a speed of signal acquisition which is comparable to parallel fluorometry.

DESCRIPTION OF THE INVENTION

This invention relates to a method and apparatus for cross-correlation frequency domain fluorometry and/or phosphorimetry. The apparatus comprises a source of electromagnetic radiation, which is typically light, as well as means for amplitude modulating the electromagnetic radiation at a first frequency. Means are also provided for directing the amplitude-modulated electromagnetic radiation at a sample for testing.

Means are also provided for detecting the luminescence (or phosphorescence) of the sample. Means are present for providing a signal coherent with amplitude modulated signals produced by the amplitude modulating means, at a second frequency, to the detecting means.

Means are also provided for modulating the gain of the detecting means or multiplying the output of the detecting means, by said signal. The gain modulating means typically comprise photomultiplier tubes. The alternative output multiplying means may comprise photodiodes and/or microchannel plates for equivalent function.

The second frequency is different from the first frequency. Means are provided for deriving a resultant signal from the electromagnetic radiation and the detecting means at a frequency of the difference between the first and second frequencies (which difference is the cross-correlation frequency), to detect phase shift and modulation changes of the luminescence from that of the source of electromagnetic radiation.

In accordance with this invention, means may be provided for sequentially performing runs of the cross-correlation frequency domain fluorometry and/or phosphorimetry by the apparatus described above at sequentially differing first and second frequencies. For example, each sequentially differing first and second frequency may differ in logarithmic order, each successive first and second frequency being for example 10 times larger than the immediately preceding first and second frequency, while, typically the cross-correlation frequency remains constant throughout the sequential performing runs. Means are provided for detecting the intensities of signal responses of the respective runs at the respective frequency which is the difference of the respective first and second frequencies used in each run, i.e., the cross-correlation frequency of each run. Means are also provided for prolonging the detecting of each said signal response at each of said differing first and second frequencies, until an integrated signal with a specific standard deviation has been acquired for each of said differing first and second frequencies.

Significant advantage is achieved by the above, since the noise associated with the measurements is not expected to be the same at all the modulation frequencies. By this invention, the measurement is performed in such a way that more time is spent when measuring at frequencies where the signal is weak, and, importantly, less time can be spent at frequencies where the signal is strong. Thus, significant savings of time can be achieved, since the measurement at each frequency is only for that necessary amount of time to achieve the desired signal to noise ratio, for a desired degree of measurement accuracy. That is to say, the acquisition is "adaptive" at each frequency in that it is possible to specify an acceptable standard deviation for the measurement. The instrument acquires data at the cross-correlation frequency of each of the differing first and second frequencies, until the specified standard deviation has been reached. Then it automatically moves on to the next set of frequencies.

Accordingly, any desired accuracy of data acquisition can be automatically obtained at the minimum time necessary for such acquisition, contrary to any of the systems of the prior art.

Preferably, means are provided for automatically executing a program of said sequentially performed runs, to reduce the time required for collecting the desired data to near its theoretical minimum for the particular apparatus used.

Also, means may be provided for synchronizing the acquisition of data waveforms sensed by the resultant signal deriving means in each run, with the phase of the signal modulating the electromagnetic radiation at the first frequency. The above means also causes the superimposing of corresponding segments of the waveforms thus sensed, to obtain an average waveform value for each run having an increased signal to noise ratio over the individual waveform segments. This process permits the linear increase of the signal to noise ratio over time in a manner which is more rapid than techniques used in the prior art.

It is also preferred for the resultant signal deriving means to comprise variable frequency digital filter means. Particularly, the preferred digital filter means is set to filter signal responses at substantially the frequency which is the difference of the respective first and second frequencies used, i.e., the cross-correlation frequency. Most preferably, the digital filter means is capable of filtering with a band which narrows over time as a signal response is detected. Such a preferred digital filter can be provided in the program of a personal computer that controls the operation of the apparatus. This digital filter starts out with wide band filtering width, and narrows as the process proceeds, as compared with an analog bandwidth filter which stays at one bandwidth forever and is not adjustable. By this invention, the variable digital filter proceeds to its filtering operation much faster due to an initial acquisition at wide bandwidth, and then narrowing down to the desired cross-correlation frequency.

Additionally, as a significant improvement, the filtering frequency at which the digital filter is set can be selected by the user through the computer software, and, if desired, can vary with different operations of this invention. Thus, if one chooses a set of first and second frequencies for the practice of this invention, the set of frequencies may typically number 10 or 20 different first and second frequencies for testing. For a single exponential decay sample one may select just a couple of frequencies. Alternatively, one may select up to 50 frequencies or more if desired. The apparatus of this invention has the capability of selecting any desired number of frequencies to measure at, and as one does so, the ratio between the time the instrument acquires data and the time the measurements take to be completed (the duty cycle) increases, contrary to instruments that are presently in the prior art. Furthermore, the frequencies can be selected on a linear, or preferably a logarithmic scale, for a better pattern of frequencies for analysis.

Additionally, the signal from the resultant signal deriving means may be automatically amplified by automatic gain means without phase and modulation changes, in those circumstances when a digital filter means is used in accordance with this invention. Such is not deemed possible when analog filter means are used, as in the prior art.

Typically, the first and second frequencies as described above are generated by frequency synthesizer means, typically phase-locked loop frequency synthesizers. While any difference between the first and second frequencies may be used, it is generally preferred to use a cross-correlation frequency of 100 to 1000 hertz. Higher cross-correlation frequencies make it possible to obtain a larger number of superimposed, corresponding segments of the waveforms, so that the average waveform value for each run having an increased signal to noise ratio is more rapidly acquired, to provide an overall increase in the speed of data acquisition.

As another advantage of this invention, one can simply set the desired cross-correlation frequency, as provided by the digital filter, to a frequency where the signal is clearly received. For example, if an instrument in accordance with this invention is installed close to a radar station, a radio station, or a laboratory where an NMR instrument is working, one can reset the first and second frequencies, and the cross-correlation frequency on the digital filter, to avoid interference problems.

Thus, measurements can be performed at a cross-correlation frequency of 10 hertz to 100 kilohertz or above, with ease.

DESCRIPTION OF THE DRAWINGS

FIG. 4 is a block diagram of the software Acquisition routine used in the fluorometer of FIG. 1;

FIG. 7 is a typical printout of data acquired by this invention.

DESCRIPTION OF SPECIFIC EMBODIMENT

Figure 1:
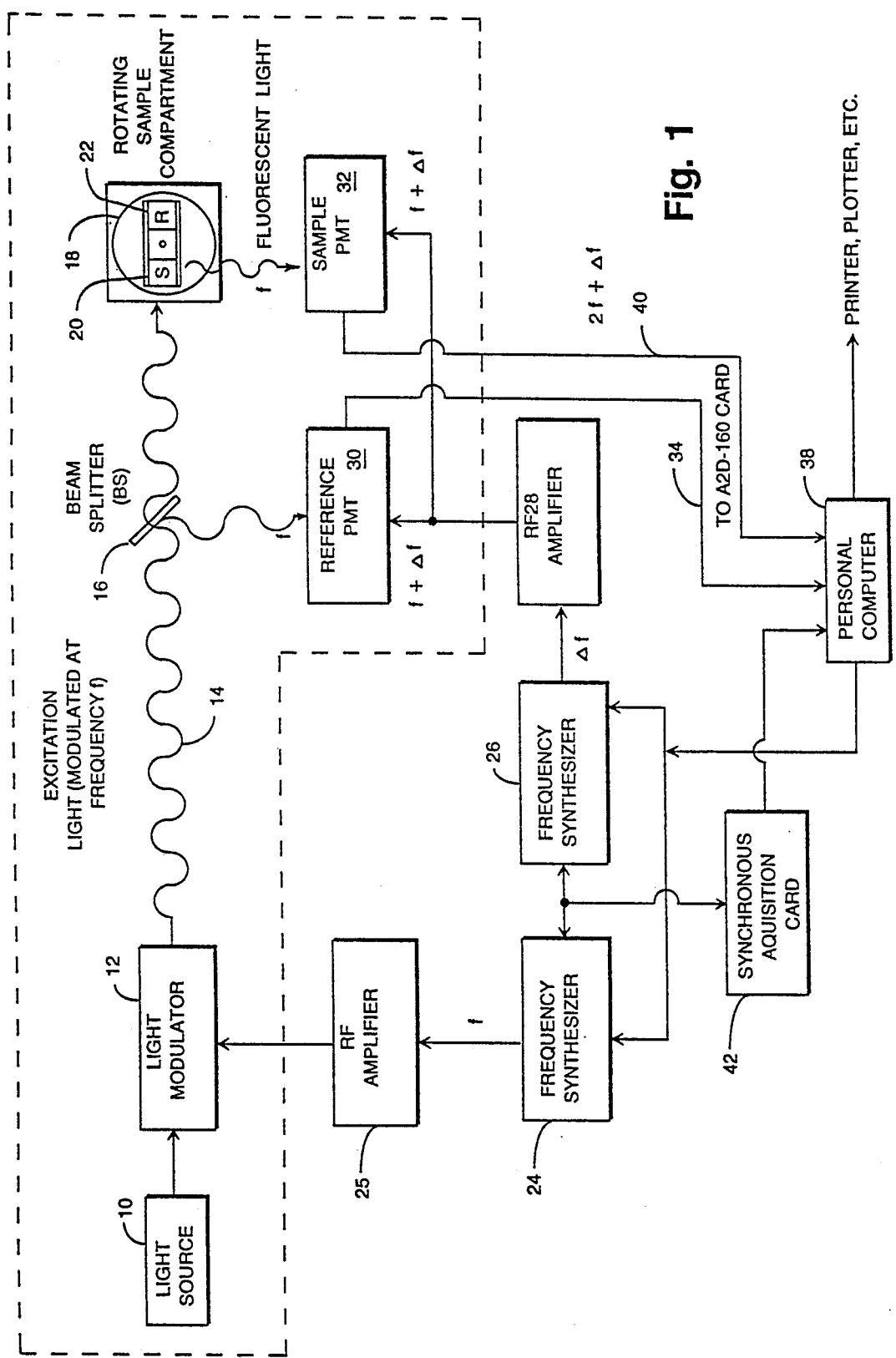
FIG. 1 is a diagrammatic view of a multi-frequency cross-correlation frequency domain fluorometer in accordance with this invention.

Referring to FIG. 1, the fluorometer of this invention is similar in structure and operation to prior art type cross-correlation frequency domain fluorometers, except as otherwise indicated herein.

A light source 10 may be a continuous wave laser or a collimated coherent or incoherent DC light source such as an arc lamp. Light from the laser 10 passes through a light modulator 12 such as a Pockels cell to provide a beam of light 14 that is amplitude modulated at a first frequency (as previously discussed). The amplitude modulated light then passes through a beam splitter 16 and into a rotating turret 18 to irradiate the sample 20 held therein. The turret can then shift by 180° to irradiate a reference sample 22.

First frequency synthesizer 24 is locked in phased relation with second frequency synthesizer 26 as shown, and imposes the first frequency on the Pockels cell 12 which, in turn, produces the beam of light 14 at said first frequency. Beam 14 may be carried by a fiber optic bundle, if desired.

Second frequency synthesizer 26, communicating through amplifier 28, modulates the gain of light detectors 30, 32 at the second frequency, which is different from the first frequency. Detectors 30, 32 may be photomultiplier tubes, photodiodes, microchannel plates, a diode array detector, a charge coupled device detector, or an avalanche photodiode system.

The signal of light beam 14 is sent by beam splitter 16 to light detector 30, while light detector 32 picks up the fluorescent light emitted by the irradiated sample 20 or 22 in turret 18, optionally through a fiber optic bundle.

Figure 6:
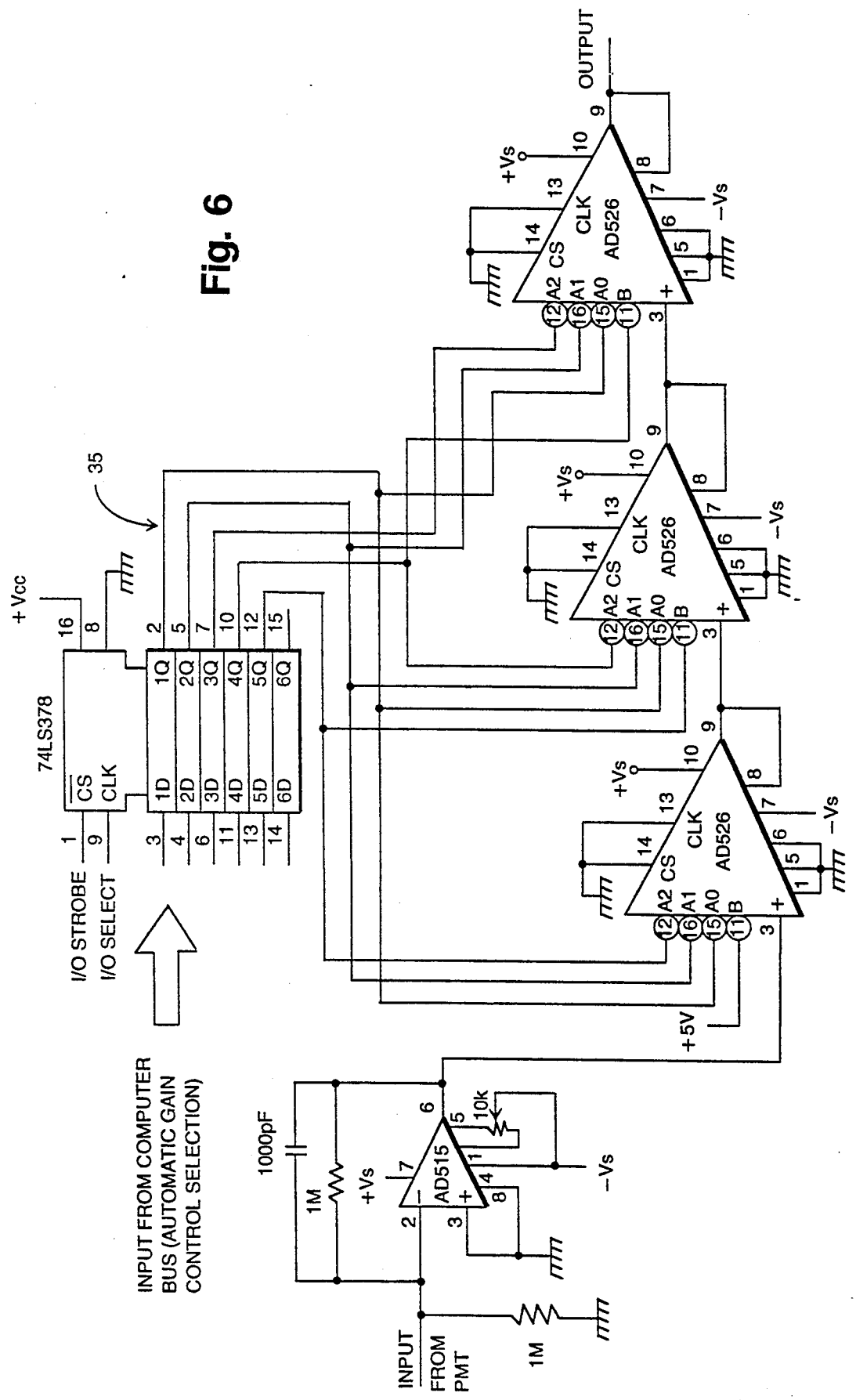
FIG. 6 is a schematic diagram of the automatic gain control circuitry, typically found in the personal computer of FIG. 1.

The signal from light detector 30 is sent via wire 34 to a digital acquisition card circuit 36 through automatic gain circuitry card 35, which typically resides in a personal computer 38. Similarly, the signal from light detector 32 is sent via wire 40 to the same automatic gain circuitry card 35 and digital acquisition card 36. Digital acquisition card 36 may be a commercial circuitry card, such as model A2D-160 from DRA Laboratories of Sterling, Virginia, or, alternatively, the Metrabyte DAS20 card. Such a card must have at least two channels of data acquisition for connection with the respective wires 34, 40 as well as the possibility of changing the gain under computer control, a digitizer with at least 12 bit resolution, a digitization rate on the order of 100 KHz, and the possibility to start the digitization cycle and setting the sampling rate under control of an external trigger. The circuitry of automatic gain card 35 may be as shown in FIG. 6.

Figure 5:
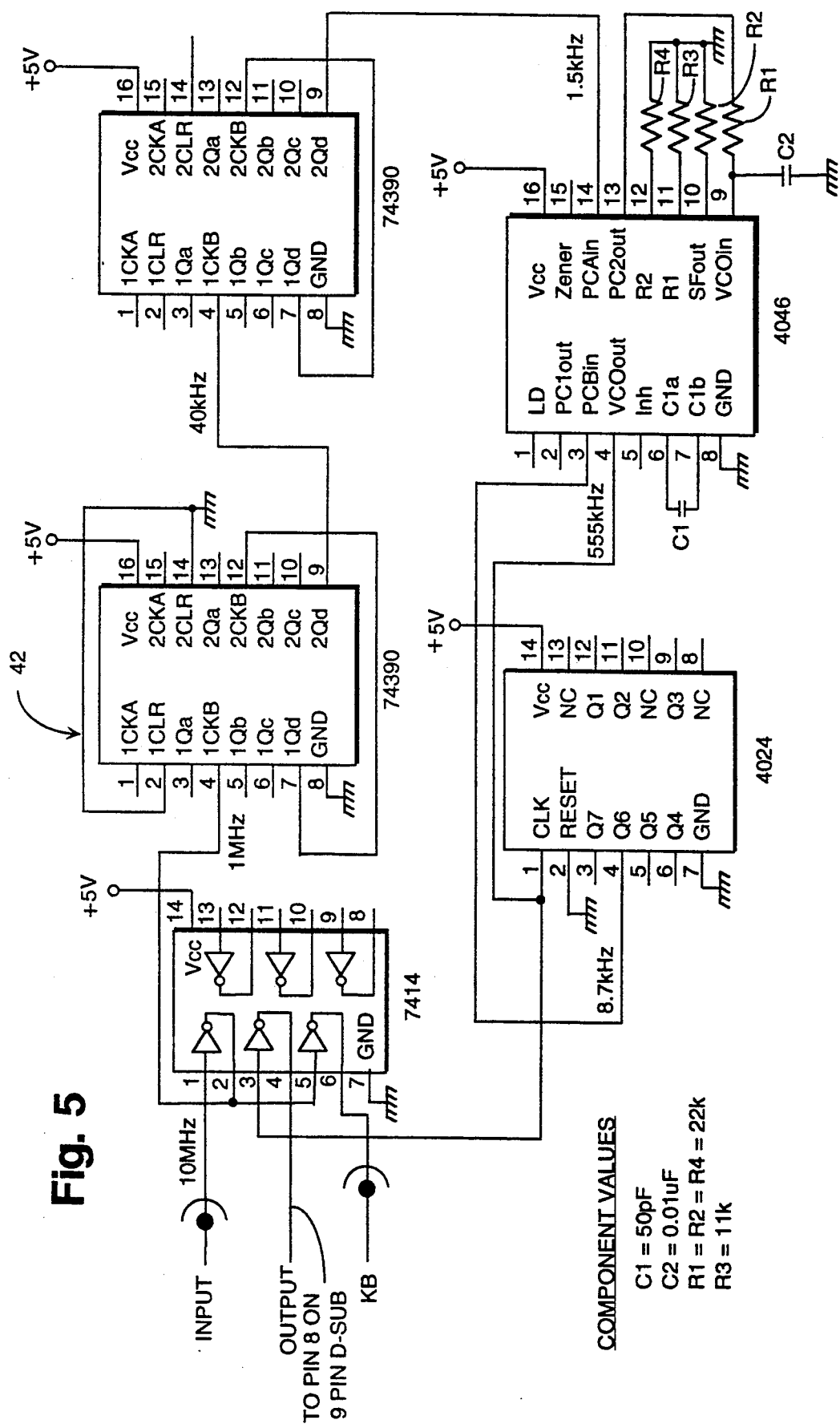
FIG. 5 is a schematic diagram of the synchronous acquisition circuitry of FIG. 1.

A synchronization signal from the frequency synthesizers is fed to card 36 through synchronous acquisition card circuit 42 as shown in FIG. 5. The purpose of this module is to provide a synchronous signal which is phase locked to the synthesizer master oscillator 24 or 26. Such synchronization greatly improves the signal to noise ratio of the measurement. Card 36 can accommodate two modules as shown by the circuitry of FIG. 5, which feature current-to-voltage converter means and computer-controlled instrumentation amplifiers for each channel of card circuitry 36.

A single wire addition to the card circuitry 36 allows to obtain the 5 volt supply to pin number 9 of the DB-connector to power the synchronization module. Card 36 fits into an 8 bit slot of the personal computer 38 and has two independent sample-and-hold circuits and one 12 bit digitizer. The maximum sampling rate is 160 KHz. As preferably operated in accordance with this invention, card 36 uses one of the computer's direct memory access channels, to relieve the central processing unit of the computer of the computer from processing data during the acquisition, so that data collection and storage occurs in the background.

As previously stated, one great advantage of this invention lies in the ability to sweep a predetermined frequency range by varying the time of measurement at each modulation frequency depending on the noise at that frequency. A set of frequencies is first selected. The frequencies are typically logarithmically spaced in the frequency range of interest. This possibility is provided by this invention as compared with the multiharmonic frequency method of the prior art. It has been previously demonstrated that the best way to sample a decay process of fluorescence or phosphorescence emission in the frequency domain is to logarithmically space frequencies around the frequency corresponding to the reciprocal of the characteristic decay time of the sample under investigation.

It is also been shown in the literature that measurement at 10 to 20 frequencies often provides the best comprise between the time of data acquisition and the information recovered. The improvement of the signal to noise ratio depends on the cube root of the number of frequencies. Therefore there is only a marginal improvement in using a 100 frequencies instead of 20. The estimated improvement, assuming that all frequencies are measured with the same signal-to-noise ratio, is about 1.7.

The signal-to-noise ratio is not constant at each frequency in the multi-harmonic techniques, since in the technique of the prior art the same acquisition time is allocated for all frequencies, but the detected signal is much weaker at higher frequencies. Instead, by this invention, great amounts of time can be saved, since in each of the serial measurements performed by this invention, less time will be spent at those frequencies where the signal is stronger, resulting in a net saving of time.

Figure 2:
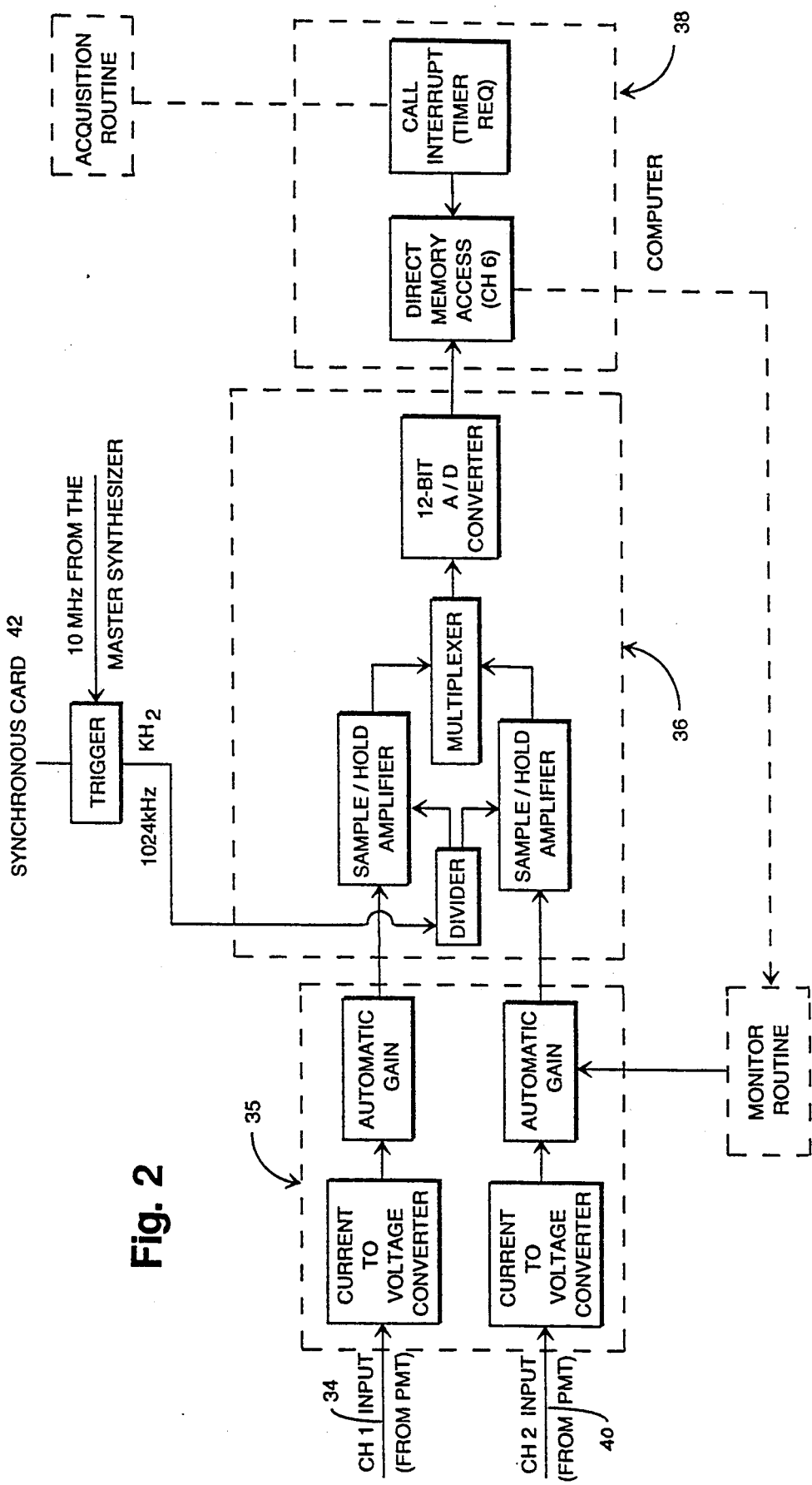
FIG. 2 is a block diagram of certain hardware and functions of the fluorometer of FIG. 1.

An additional advantage of this invention relates to the digital processing of the signal. A first operation performed on the digitized waveform is the "folding" operation by which successive periods of the cross-correlation frequency waves are arranged exactly in phase, as a part of the monitor routine shown in FIG. 3, and also FIG. 2. Such a software process is available to the prior art, and is discussed for example in Malmstadt, et al., Digital and Analog Data Conversions, Part III, W. A. Benjamin, Inc. (1973).

Figure 3:
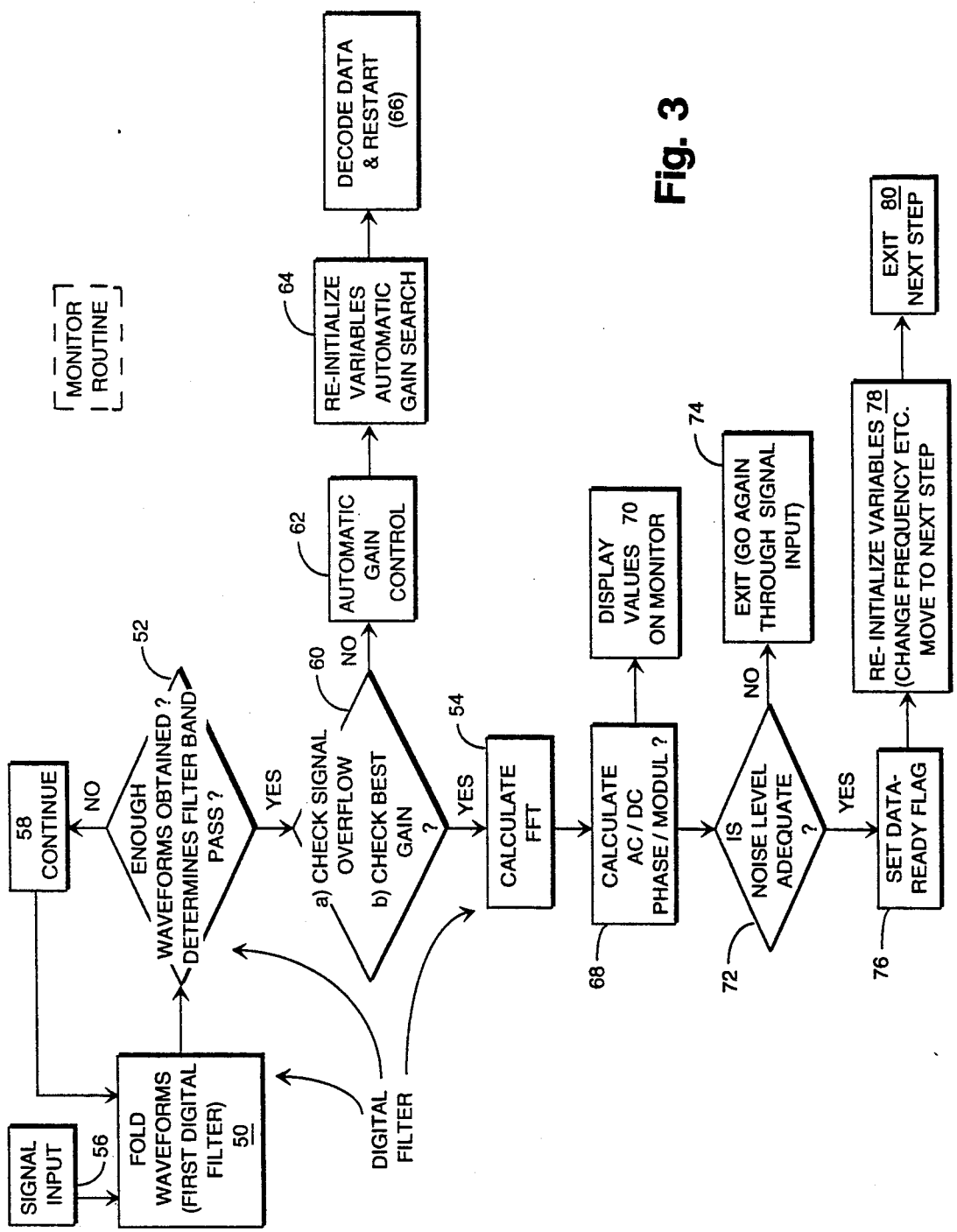
FIG. 3 is a block diagram of the software Monitor routine used in the fluorometer of FIG. 1.

As more waves are averaged, the signal to noise ratio increases linearly with the number of waves rather than with the square root of the number of waves averaged. This is due to the fact that every signal which is not exactly in phase with the cross-correlation signal will be cancelled out as more waves are averaged, so that a digital filter function is provided to the Monitor routine, particularly by steps, 50, 52 and 54 of the monitor routine (FIG. 3). The equivalent bandwidth of this digital filter is a function of time, and the signal to noise ratio will increase rapidly.

For example, assuming that the basic waveform to be measured is at 100 Hz, after folding for one second, all the frequency components higher than 1 Hz will be averaged out, while those having frequencies below 1 Hz will remain. For the same reason, after 5 seconds integration, only frequency components below 0.2 Hz will contribute to the signal. The equivalent Q of this digital filter, (defined as the value of center frequency divided by the bandwidth) is then 500, and the Q increases if the cross-correlation frequency is increased. The new digital acquisition mode makes the selection of the cross-correlation frequency very simple. Therefore, very high Q filters, with no center frequency drift and gain distortion, can easily be implemented.

It is clear from the above that a synchronous (to the cross-correlation frequency) signal is desirably available to trigger the digitization process, as provided by synchronous card circuitry 42.

Another advantage that the digital filter function of this invention has, compared with an equivalent analog filter, is that data acquisition can start immediately after the new frequency has been selected, since the filter Q is very low at early times. Instead, using an analog filter with a Q of 80 at 40 Hz requires at least 2-3 seconds before the signal has reached a steady-state value. Thus, in this situation, a fast frequency sweep cannot be efficiently performed.

Referring further to the monitor routine, the waveforms of the signal input 56 are folded (reference numeral 50) by a known software routine. It is determined whether enough waveforms are obtained, which also determines the filter band pass 52. If enough waveforms have not been obtained, the process is recycled back 58 to fold more waveforms 50. If enough waveforms have been obtained, there is a checking process 60 for signal overflow and the best gain. If the answer is no, after automatic gain control 62, a known routine is provided (64) for reinitializing variables, i.e. providing an automatic gain search. The collected data is discarded, and the system restarted (66) by further signal input 56 to the waveform folding 50.

If, however, the answer is yes to the check signal overflow and check best gain 60, a fast Fourier transform is calculated (54). The AC/DC phase modulation 68 is performed, and the values are displayed on a monitor 70. Also, the adequacy of the noise level 72 is determined. If not, through an exit 74 the signal input 56 is reactivated for more waveform folding. If the answer is yes, a data-ready flag 76 is set. The variable are reinitialized 78 to change frequencies and go on to the next step of the process, which may be operation at a different frequency, or activation of turret 18 to switch from one sample to the other 20, 22, or vice versa. And then the next step 80 proceeds.

Typically, the process of this invention can proceed as follows:

1. The light shutters of the apparatus (conventional equipment) are closed, and a background reading is acquired for about 5 seconds, which is typically optimal.

2. The sample 20 is then illuminated, and data acquisition starts immediately. At every second the data acquired are transferred to a working vector without interrupting the acquisition process which proceeds in the background. Noise monitor 72, a conventional software expedient, estimates the amount of noise in the waveform acquired and compares it with a preselected value. Acquisition can be as short as 1 second for bright samples.

3. The acquisition continues until the estimated noise is below an acceptable value. Then, a new frequency is selected per steps 76, 78, 80 from a preferably logarithmically-spaced frequency series, and the process starts again, continuing step by step until all frequencies of the set have been measured.

4. Then a reference compound 22 is illuminated, and the same process as for the sample is performed, step-by-step, until all frequencies have been measured.

5. The phase and demodulation ratio of the sample are calculated with respect to the phase and demodulation ratio of the reference compound.

The entire process is very efficient, and lasts for typically about 3 minutes for medium intensity sample of 10 frequencies. If samples are very bright, the entire process can terminate in less than 1 minute for the acquisition of 10 frequencies.

To take advantage of the new capabilities offered by this invention, it is preferred for data collection to proceed without loss of synchronization, and data are collected using a large number of points for each waveform. In addition, the waveforms should be at the highest possible frequency compatible with the speed of the digital card 36 used herein. Preferably, cross-correlation frequencies up to 500 Hz are particularly desirable.

The minimum number of points per waveform that provides accurate phase and modulation determination is on the order of 128 points. The power of 2 is necessary for the application of the Fast Fourier transform 54. Since at least two different signals must be acquired, one from the sample photomultiplier 32 and the other from the reference photomultiplier 30, the number of points to be sampled per second is typically about 126,200. This is approximately the maximum digitization speed of the digital acquisition card 36 used herein and described above.

It is also desirable to have the capability to continuously display on the screen the values of the voltages at each detector 30, 32, the values of the modulation of the sample and reference 20, 22, and the phase difference between sample and reference as computed by the software. This feature is important for the setting of the instrument prior to each measurement and for monitoring the measurement during data acquisition, since no other information regarding the amount of light reaching the detectors may be available. In addition, it is desirable to have a way to monitor the noise of the signal in order to select the proper integration at each frequency.

In order to provide a monitor of the instrument signals and a noise monitor during data acquisition, among other reasons, the software used in this embodiment preferably also utilizes the following features:

1. Data acquisition proceeds at constant speed in the background using the direct memory access capabilities of the IBM personal computer (an IBM-compatible computer can be utilized as well; specifically, every computer utilizing a CPU of the Intel's iAPx86 family microprocessor starting with the 82086 and including the 80386 and the 80486.)

2. The digitized data are stored in a "circular buffer" that contains a maximum of 64000 points.

3. At each computer clock tick (18 times per second) an interrupt routine is activated that checks how much of the data buffer has been filled.

4. If more than half of the data buffer has been filled, half of the buffer is copied and folded in a working array that contains 256 points. The signal is folded in such a way that each period of the waveform is added exactly in phase to the previously stored waveform. When the second half of the buffer is filled, then data are processed from this part of the buffer while the first part is receiving the new data from the digitizer.

5. When a certain number of waveforms have been folded then the Monitor routine (FIG. 3) is called. Generally the number of waveforms to be folded is chosen in such a way that the Monitor routine is called every 0.5 seconds.

6. The Monitor routine performs a series of tests on the signal; it checks for signal overflow, determines the most appropriate gain for the amplifiers connected with each channel, and calculates the fast Fourier transform of the signal to determine the value of the phase and modulation of the signal from the two detectors.

7. Depending on the operation condition of the instrument, the Monitor routine passes data to the Acquisition routine (FIG. 4) of the main program for accumulation and storage and display.

8. The folding of 64000 data points, the fast Fourier transform (FFT) calculation, and the screen display of the different instrument parameters require about 0.4 to 0.6 second on a 386 computer with math coprocessor. Since this operation should be performed every 0.5 to 1 second, clearly there is very little time for performing any other task such is keyboard entry and display, driving the instrument motors and reading or writing disk files.

9. For monitoring purpose only, it is not necessary to collect so many data points and to calculate the FFT on 128 points. During data acquisition the computer is not performing other operations such as moving motors or writing disk files. Therefore two modes of operations have been implemented: one that read one every 8 data points and performs a FFT on 16 points only and a second mode of operation in which all data points are processed.

10. The Monitor routine (FIG. 3) communicates with the rest the of the using a series of semaphores. They signal to the monitor program what is the status of the instrument. For example, when the instrument is not acquiring data, the semaphore signals to use one every 8 points of the data collected instead of all data points. Other semaphores signal that a disk reading or writing is taking place or that a motor is moving. Motor movement should be smooth, so that this operation should not be interrupted. Also, all graphics operations require more time and that is signalled to the Monitor routine.

FIG. 7 discloses a typical phase and modulation curve, expressed in standard manner for fluorometry, which may be achieved by the apparatus and method of this invention. Specifically, an amplitude modulated, three hundred watt xenon arc lamp was used as light source 10 to measure the lifetime of excited Lysozime (from Sigma Chemical Co.) in a 50 mM phosphate buffer at 25° C. The three hundred nanometer excitation wavelength was selected through a monochromator carried on the fluorometer. The reference sample 22 was glycogen dispersion which scatters light rather than absorbing it. A Corning WG-320 high-pass filter was used in emission. Two lifetimes, 1.2 ns and 3.4 ns were measured, associated to 61% and 39% fractional intensity respectively. The various points on the scale represent the results of sequential fluorometry readings at different frequencies as described herein. The acquisition time for all the points shown on the chart was less than 150 seconds. The points on the curve indicated by squares pertain to the modulation scale, expressed in the known arbitrary units. The points on the curve marked by X relate to the phase scale, expressed in degrees.

The invention may be used to perform any known fluorometry or phosphorimetry measurements, particularly fluorescence or phosphorescence decay, anisotropy decay of fluorescence of phosphorescence, time-resolved spectra, resolution of lifetime kinetics, resolution of spectra in mixtures, and the like.

The above has been offered for illustrative purposes only, and is not intended to limit the scope of the invention of this application, which is as defined in the claims below.

That which is claimed is:

1. In apparatus for cross-correlation frequency domain fluorometry-phosphorimetry, which comprises:

a source of electromagnetic radiation;

means for amplitude modulating the electromagnetic radiation at a first frequency;

means for directing the amplitude-modulated electromagnetic radiation at a sample;

means for detecting the luminescence of the sample;

means for providing a signal coherent with amplitude modulated signals produced by said amplitude modulating means, at a second frequency, to said detecting means;

means for modulating the gain of said detecting means, or multiplying the output of said detecting means, by said signal;

said second frequency being different from said first frequency; and means for deriving a resultant signal from said electromagnetic radiation and said detecting means at a frequency of the difference between said first and second frequencies, to detect phase shift and modulation changes of said luminescence from that of said electromagnetic radiation;

the improvement comprising, in combination: means for sequentially performing runs of said cross-correlation frequency domain fluorometry-phosphorimetry at sequentially differing first and second frequencies; means for detecting the intensities of signal responses of said runs at the respective cross-correlation frequency which is the difference of the respective first and second frequencies used in each run; and means for prolonging the detecting of each signal response at each of said differing first and second frequencies, until an integrated signal with a specified standard deviation has been acquired at each of said differing first and second frequencies.

2. The apparatus of claim 1 in which means are provided for automatically executing a program of sequentially performed runs.

3. The apparatus of claim 1 in which means are provided for synchronizing the acquisition of data waveforms sensed by said resultant signal deriving means in each run with the phase of the signal modulating the electromagnetic radiation at said first frequency, and for superimposing corresponding segments of said waveforms thus sensed to obtain an average waveform value for each run having an increased signal to noise ratio over the individual waveform segments.

4. The apparatus of claim 1 in which said resultant signal deriving means comprises variable frequency digital filter means.

5. The apparatus of claim 4 in which said digital filter means is set to filter signal responses at substantially the frequency which is the difference of the respective first and second frequencies used.

6. The apparatus of claim 5 in which said digital filter means is capable of filtering with a bandwidth narrowing over time as a signal response is detected.

7. The apparatus of claim 6 in which the signal from said resultant signal deriving means is automatically amplified by automatic gain means without phase and modulation changes.

8. The apparatus of claim 1 in which the first and second frequencies are each generated by frequency synthesizer means, the frequency of the difference between said first and second frequencies being essentially 50 to 1000 hertz.

9. In apparatus for cross-correlation frequency domain fluorometry-phosphorimetry, which comprises:
a source of electromagnetic radiation;
means for amplitude modulating the electromagnetic radiation at a first frequency;
means for directing the amplitude-modulated electromagnetic radiation at a sample;
means for detecting the luminescence of the sample;
means for providing a signal coherent with amplitude modulated signals produced by said amplitude modulating means, at a second frequency, to said detecting means;
means for modulating the gain of said detecting means or multiplying the output of said detecting means by said signal;
said second frequency being different from said first frequency; and means for deriving a resultant signal from said electromagnetic radiation and said detecting means at a frequency of the difference between said first and second frequencies, to detect phase shift and modulation changes of said luminescence from that of said electromagnetic radiation;
the improvement comprising, in combination: means for automatically and sequentially performing runs of said cross-correlation frequency domain fluorometry-phosphorimetry at sequentially differing first and second frequencies; means for detecting the intensities of signal responses of said runs at the respective cross-correlation frequency which is the difference of the respective first and second frequencies used in each run; and means for prolonging the detecting of each said signal response at each of said cross-correlation frequencies until an integrated signal with a specific standard deviation has been acquired at each of said different cross-correlation frequencies; said resultant signal deriving means comprising variable frequency digital filter means capable of being set to filter signal responses at substantially the cross-correlation frequencies.

10. The apparatus of claim 9 in which said digital filter means is capable of filtering with a bandwidth narrowing over time as a signal response is detected.

11. The apparatus of claim 10 in which the signal from said resultant signal deriving means is automatically amplified by automatic gain means without phase and modulation changes.

12. The apparatus of claim 11 in which the first and second frequencies are each generated by frequency synthesizer means, the frequency of the difference between said first and second frequencies being essentially 50 to 1000 hertz.

13. The apparatus of claim 12 in which means are provided for synchronizing the acquisition of data waveforms sensed by said resultant signal deriving means in each run with the phase of the signal modulating the electromagnetic radiation of said first frequency, and for superimposing corresponding segments of said waveforms thus sensed to obtain an average waveform value for each run having an increased signal to noise ratio over the individual waveform segments.

14. In apparatus for cross-correlation frequency domain fluorometry-phosphorimetry, which comprises:
a source of electromagnetic radiation;
means for amplitude modulating the electromagnetic radiation at a first frequency;
means for directing the amplitude-modulated electromagnetic radiation at a sample;
means for detecting the luminescence of the sample;
means for providing a signal coherent with amplitude modulated signals produced by said amplitude modulating means, at a second frequency, to said detecting means;
means for modulating the gain of said detecting means or multiplying the output by said detecting means by said signal;
said second frequency being different from said first frequency; and means for deriving a resultant signal from said electromagnetic radiation and said detecting means at a frequency of the difference between said first and second frequencies, to detect phase shift and modulation changes of said luminescence from that of said electromagnetic radiation;
the improvement comprising, in combination: means for synchronizing the acquisition of data waveforms sensed by said resultant signal deriving means in each run, with the phase of the signal modulating the electromagnetic radiation at said first frequency, and for superimposing corresponding segments of said waveforms thus sensed to obtain an average waveform value for each run having an increased signal to noise ratio over the individual waveform segments, said synchronizing means comprising variable bandwidth digital filter means.

15. The apparatus of claim 14 in which said first and second frequencies are each generated by frequency synthesizer means, the frequency of the difference between said first and second frequencies being essentially 100 to 1000 hertz.

16. In a method for frequency domain cross-correlation fluorometry-phosphorimetry which comprises the steps of:
providing a source of electromagnetic radiation;

amplitude modulating the electromagnetic radiation at a first frequency;

directing the amplitude-modulated electromagnetic radiation at a sample;

detecting with a detector the luminescence of the sample while modulating the gain of said detector or multiplying the output of said detector with a signal at a second frequency to said detector; with said signal at a second frequency being coherent with the modulation of said electromagnetic radiation and said second frequency being different from said first frequency; and deriving a resultant signal from said electromagnetic radiation and said detector at a frequency of the difference between said first and second frequencies, to detect phase shift and modulation of said luminescence from that of said electromagnetic radiation;

the improvement comprising, in combination: sequentially and automatically performing runs of said cross-correlation frequency domain fluorometry-phosphorimetry at sequentially differing values of said first and second frequencies; detecting the intensities of signal responses of said runs at the respective frequency which is the difference of the respective first and second frequencies of each run; and prolonging the time of said detecting of each signal response at each of said different first and second frequencies until an integrated signal with a specific standard deviation has been acquired at each of said differing first and second frequencies.

17. The method of claim 16 including the step of synchronizing the acquisition of data waveforms sensed by deriving said resultant signal, and superimposing corresponding segments of said waveforms to obtain an average waveform value for each run having an increased signal to noise ratio over the individual waveform segments.

18. The method of claim 17 in which said resultant signal is derived by means comprising variable frequency digital filter means.

19. The method of claim 18 in which said digital filter means is set to filter signal responses at substantially a third frequency which is essentially the difference of the respective first and second frequencies used.

20. The method of claim 19 in which said third frequency is at least substantially 100 to 1000 hertz.

21. The method of claim 19 in which said digital filter means is capable of filtering with a narrowing over time bandwidth as a signal response is detected.

22. The method of claim 19 in which the resultant signal is automatically amplified by automatic gain means without phase and modulation changes.

23. The method of claim 19 in which said first and second frequencies are varied from run to run on a logarithmic scale, with the difference between said first and second frequencies being substantially constant.

24. In a method for frequency domain cross-correlation fluorometry-phosphorimetry which comprises the steps of:

providing a source of electromagnetic radiation;

amplitude modulating the electromagnetic radiation at a first frequency;

directing the amplitude-modulated electromagnetic radiation at a sample;

detecting with a detector the luminescence of the sample while modulating the gain or multiplying the output of said detector with a signal at a second frequency to said detector; with said signal at a second frequency being coherent with the modulation of said electromagnetic radiation and said second frequency being different from said first frequency; and deriving a resultant signal from said electromagnetic radiation and said detector at a frequency of the difference between said first and second frequencies, to detect phase shift and modulation of said luminescence from that of said electromagnetic radiation;

the improvement comprising, in combination:

sequentially and automatically performing runs of said cross-correlation frequency domain fluorometry at sequentially differing values of said first and second frequencies; in which said resultant signal is derived by means comprising variable frequency digital filter means set to filter signal responses at substantially a third frequency which is the difference of the respective first and second frequencies used.

25. The method of claim 24 in which said third frequency is substantially 100 to 1000 hertz, said digital filter means being capable of filtering with a narrowing over time bandwidth as a signal response is detected.

26. The method of claim 24 in which the signal from said resultant signal deriving means is automatically amplified by automatic gain means without phase change.

27. The method of claim 24 including the step of synchronizing the acquisition of data waveforms sensed by deriving said resultant signal, and superimposing corresponding segments of said waveforms to obtain an average waveform value for each run having an increased signal to noise ratio over the individual waveform segments.

* * * * *